United States Patent [19]
Lansky

[11] Patent Number: 6,060,063
[45] Date of Patent: May 9, 2000

[54] PHYTOESTROGEN SUPPLEMENTS PREPARED FROM POMEGRANATE MATERIAL INCLUDING POMEGRANATE SEEDS

[76] Inventor: Ephraim Philip Lansky, 3 Horev, Haifa 31060, Israel

[21] Appl. No.: 09/285,703

[22] Filed: Apr. 5, 1999

Related U.S. Application Data

[63] Continuation-in-part of application No. 08/777,895, Dec. 31, 1996, Pat. No. 5,891,440.
[51] Int. Cl.⁷ .................................................. A61K 35/78
[52] U.S. Cl. ........................................ 424/195.1; 514/874
[58] Field of Search .......................... 424/195.1; 514/874

[56] References Cited

PUBLICATIONS

Schubert et al. J. Ethnopharmocol. vol. 66, No. 1, pp. 11–17, abstract enclosed, 1999.

*Primary Examiner*—Leon B. Lankford, Jr.
*Assistant Examiner*—Christopher R. Tate
*Attorney, Agent, or Firm*—Mark M. Friedman

[57] ABSTRACT

A phytoestrogen supplement and methods of preparation are described. The basis of the oral phytoestrogen supplement was a preparation of the pomegranate material, preferably pomegranate seeds, which were contacted with an appropriate solvent as described below, preferably including water and ethanol. Preferably, the supplement also included an herbal mixture, including schizandra berries and Chinese asparagus root, and most preferably including Chinese licorice root and Chinese angelica root. The phytoestrogen supplement can also be prepared from pomegranate material alone without the addition of other herbals, which involves fermenting the pomegranate material including the pomegranate seeds. The basis of topical phytoestrogen supplements was a mixture of a preparation of the pomegranate material, preferably pomegranate seeds, which were pressed as described below to produce pomegranate oil, and of the coconut milk. Preferably, the supplements also included schizandra berries and Chinese asparagus root.

4 Claims, No Drawings

PHYTOESTROGEN SUPPLEMENTS PREPARED FROM POMEGRANATE MATERIAL INCLUDING POMEGRANATE SEEDS

This is a Continuation-in-Part Application of U.S. patent application Ser. No. 08/777,895, filed on Dec. 31, 1996, now U.S. Pat. No. 5,891,440.

FIELD AND BACKGROUND OF THE INVENTION

The present invention relates to phytoestrogen supplements and, more particularly, to phytoestrogen supplements derived from botanical sources which can be administered in a variety of ways.

Steroidal estrogens are typically derived from animal sources and are used to treat conditions such as menopause. Menopause occurs as ovarian function gradually declines, leading to the cessation of ovulation, menstruation and finally secretion of estrogen by the ovaries. The decline and cessation of estrogen secretion leads to a number of symptoms, including hot flashes, mood disturbances such as depression, atheromatous disease and osteoporosis.

Although animal-derived steroidal estrogens, such as estradiol, estratiol and estrone, can be successfully used to treat these symptoms, many women are reluctant to take these substances, and many medical professionals are equally reluctant to prescribe them. These estrogens have been linked to an increase in cancer in women to whom they were administered. Thus, it would be advantageous to find a substance or group of substances which mimic the desirable effects of estrogens, namely the cessation of symptoms associated with menopause, yet which are not carcinogenic.

Phytoestrogens are non-steroidal compounds found in a variety of plants, which exert estrogenic effects in animals. Phytoestrogens from botanical materials may reduce the frequency of hot flashes in Japanese women. Such phytoestrogens were shown to be excreted at a high level in the urine of these women, and are associated with a high level of intake of soy products which contain phytoestrogens [Adlercreutz, H., Hamalainen, E., Gorbach, S. and B. Goldin, *The Lancet*, 1992, 339:1233]. Estrogenic effects were shown in postmenopausal women after dietary supplementation with soy flour and linseed, which contain phytoestrogens [Wilcox, G. Wahlqvist, M. L., Burger, H. G. and G. Medley, *British Medical Journal*, 1990, 301:905–6].

Such phytoestrogens are known to be present in pomegranate seeds. The level of phytoestrogens was measured by preparing an acetone extract of the pomegranate seeds and then subjecting this extract to HPLC (High Performance Liquid Chromatography) [Moneam, N. M. A., El Sharaky A. S. and M. M. Radreldin, *Journal of Chromatography*, 1988, 438:438–442]. Both non-steroidal phytoestrogens and steroidal estrogen were found in the extract.

The estrogenic activity of another preparation of pomegranate seeds has also been described in ovariectomized mice and immature rabbits [A. Sharaf and S. A. R. Nigm, *Journal of Endocrinology*, 1964, 29:91–92]. This preparation was made by extracting the pomegranate seeds with ether and showed clear estrogenic activity in both the mice and the rabbits, specifically measured by cornification of the vaginal cells and an increase in uterine weight.

The presence of sex hormone-like substances in milk from immature coconuts has also been demonstrated [B. Punghmatharith, *Warasan Songkhla Nakkharin*, 1988, 10:221–226]. Furthermore, these substances were shown to have estrogenic activity in rats, altering the uterine growth in these animals.

As noted above, a number of botanical materials have been shown to contain phytoestrogens, such as soybeans from *Soja max*. Other sources of phytoestrogens include *Glycyrrhiza glabrata* or liquorice, *Medicago sativa* or alfalfa and *Malus sylvestris* or apple [K. R. Price and G. R. Fenwick, *Food Additives and Contaminants*, 1985, 2:73–106].

Although such phytoestrogens have only recently come to the attention of Western medicine, the use of plants to treat female patients for conditions related to the reproductive system has been shown in Chinese medicine for hundreds of years. For example, Chinese angelica root (*Angelica sinensis*), Chinese licorice root (*Glycyrrhizae uralensis*), Chinese asparagus root (*Asparagus lucidus*) and schizandra berries (*Schizandra chinesis*) have all been used in Chinese herbal medicine to treat female patients, specifically for complaints concerning the reproductive system [*Chinese Tonic Herbs*, by R. Teeguarden, Japan Publications, New York, 1985]. Typically, preparations containing these botanical materials were given orally, and were considered to be highly effective.

Other examples of botanical preparations include skin creams. A cream for oily skin has been prepared which includes a carbonic acid extraction of rinds and seeds of pomegranates, as described in USSR Patent No. 1,602,533. However, such an extract has the disadvantage of being prepared with carbonic acid, rater than with a less toxic solvent. Furthermore, no suggestion was made that such an extract could also be used as an oral phytoestrogen supplement, rather than simply as a topically applied skin cream. Certainly, if such an extract were to be used orally, a less toxic solvent would be needed.

There is thus a widely recognized need for, and it would be highly advantageous to have, an oral phytoestrogen supplement prepared from pomegranate material, such as pomegranate seeds, as well as a skin cream prepared from such material. Furthermore, it would be advantageous to include other botanical sources of phytoestrogens for increased effectiveness of the oral supplement and skin cream. Finally, it would be advantageous to use these sources of phytoestrogens in a vaginal cream.

SUMMARY OF THE INVENTION

According to the present invention there is provided an oral phytoestrogen supplement, as well as a method of preparing the oral phytoestrogen supplement, including the step of contacting pomegranate material with an appropriate solvent to form a pomegranate extract, the extract being suitable for oral administration. Preferably, the solvent includes water and ethanol. Also preferably, the pomegranate material includes crushed pomegranate seeds.

According to preferred embodiments of the present invention, the method further includes the steps of: (b) contacting a herbal mixture with water to form an aqueous extract, the herbal mixture including schizandra berries and Chinese asparagus root; and (c) mixing the aqueous extract with the pomegranate extract to form a mixture.

According to further preferred embodiments of the present invention, the method further includes the steps of: (d) filtering the mixture to remove solid material to form a filtered mixture; (e) heating the solid material until the solid material is substantially carbonized, forming carbonized solid material; (f) extracting the carbonized solid material with water to form a second aqueous extract; and (g) mixing the aqueous extract with the filtered remixture to form a second mixture. Preferably, the herbal mixture farther includes Chinese licorice root and Chinese angelica root. Also preferably, the ratio of the Chinese licorice root to the Chinese asparagus root to the Chinese angelica root to the schizandra berries is about 2:2:1:2. Most preferably, a weight of the Chinese licorice root is about 300 g, a weight of the Chinese asparagus root is about 300 g, a weight of the Chinese angelica root is about 150 g and a weight of the schizandra berries is about 300 g.

According to another embodiment, there is provided an ointment and a method of preparing die ointmient, including the steps of (a) preparing pomegranate oil by pressing pomegranate seeds; and (b) mixing the pomegranate oil with coconut milk to form a mixture.

According to preferred embodiments of the present invention, the method further includes the steps of: (c) preparing an extract of Chinese asparagus root and schizandra berries by contacting the Chinese asparagus root and the schizandra berries with ethanol; and (d) adding the extract to the mixture. Most preferably, the method further includes the step of: (e) adding a pharmaceutically appropriate carrier to the mixture. Preferably, the pharmaceutically appropriate carder includes beeswax and cocoa butter, or alternatively and preferably, hydrophilic lanolin. Also preferably, a ratio of the pomegranate oil to the coconut milk to the extract of the Chinese asparagus root to the extract of the schizandra berries is about 40:20:3:3. Most preferably, a weight of the pomegranate oil is about 40 g, a weight of the coconut milk is about 20 g, a weight of the extract of the Chinese asparagus root is about 3 g and a weight of the extract of the schizandra berries is about 3 g.

According to yet another embodiment, there is provided a method of preparing a phytoestrogen supplement, comprising the step of contacting pomegranate material with a solvent selected from the group consisting of water and ethanol to form a pomegranate extract. Preferably, the pomegranate material includes crushed pomegranate seeds. More preferably, the method further includes the steps of: (b) contacting a herbal mixture with water to form an aqueous extract, the herbal mixture including schizandra berries and Chinese asparagus root; and (c) mixing the aqueous extract with the pomegranate extract to form a mixture. Most preferably, the method further includes the steps of: (d) filtering the mixture to remove solid material and to form a filtered mixture; (e) heating the solid material until the solid material is substantially carbonized, forming carbonized solid material; (f) extracting the carbonized solid material with water to form a second aqueous extract; and (g) mixing the aqueous extract with the filtered mixture to form a second mixture.

According to still another embodiment of the present invention, there is provided a method of preparing an oil combination, the method composing the steps of: (a) preparing pomegranate oil by pressing pomegranate seeds; (b) preparing at least one seed oil selected from the group consisting of barley seed oil, cherry kernel oil and fenugreek seed oil; and (c) mixing the pomegranate oil with the at least one seed oil to form a mixture as the oil combination.

According to yet another embodiment of the present invention, there is provided a method of preparing a phytoestrogen suspension from pomegranate material, the pomegranate material including seeds, the method comprising the steps of: (a) fermenting the pomegranate material to form a fermented pomegranate material; (b) removing the seeds from the fermented pomegranate material; (c) pressing the seeds to form pomegranate seed oil and a seed cake; (d) removing ethanol from the fermented pomegranate material to form a first liquid, (e) drying the first liquid to form a first powder; and (f) combining the first powder and the pomegranate seed oil to form the phytoestrogen suspension.

According to still another embodiment of the present invention, there is provided a method for preparing a nutraceutical seed cake, the method comprising the steps of: (a) preparing pomegranate oil and a pomegranate seed cake by pressing pomegranate seeds; (b) preparing at least one seed oil and at least one other seed cake by pressing seeds selected from the group consisting of barley seeds, cherry kernels and fenugreek seeds; and (c) mixing the pomegranate seed cake and the at least one other seed cake to form the nutraceutical seed cake.

DESCRIPTION OF THE PREFERRED EMBODIMENTS

The present invention is of phytoestrogen supplements which can be administered in a variety of ways, including topically and orally. Specifically, the compositions of the present invention can be used to relieve symptoms in menopausal women, including hot flashes, osteoporosis and mood disturbances when given orally, and vaginal dryness and lack of skin tone when administered topically, as well as any other effects related to the lack of estrogen.

The invention is illustrated by the following examples, which describe the preparation and use of phytoestrogen supplements to relieve symptoms in menopausal or postmenopausal women.

EXAMPLE 1

Method of Preparation of Phytoestrogen Supplements

The following botanical materials were used to prepare various embodiments of the phytoestrogen supplement, pomegranate material, preferably pomegranate seeds (*Punica granatum*), schizandra berries (*Schizandra chinensis*), Chinese licorice root (*Glycyrrhizae uralensis*), Chinese asparagus root (*Asparagus lucidus*) and Chinese angelica root (*Angelic sinensis*). The pomegranate seeds were preferably fresh with intact juice sacs. The schizandra berries were preferably dried. The three roots, Chinese licorice root, Chinese asparagus root and Chinese angelica root, were all preferably dried and cut.

The basis of the phytoestrogen supplement of Example 1 was a preparation of the pomegranate material, preferably pomegranate seeds, which were contacted with an appropriate solvent as described below, preferably including water and ethanol, to form an extract. If the supplement was intended as an oral phytoestrogen supplement, the extract was suitable for oral administration. For example, to make such an extract suitable for oral administration, the solvents were substantially non-toxic to the subject, so that there should not be an untoward level of adverse side effects, such as toxicity, irritation, allergy or hypersensitivity responses. The level of any such side effects should be commensurate with acceptable risk/benefit ratios. Examples of such substantially non-toxic solvents include water and ethanol. Otherwise, the extract is preferably prepared by contacting a preparation of the pomegranate material, preferably pomegranate seeds, with a solvent selected from the group consisting of water and ethanol, although other solvents could be used in addition to, or as replacements for, these solvents.

Preferably, the supplement also included a herbal mixture, including schizandra berries and Chinese asparagus root, and most preferably including Chinese licorice root and Chinese angelica root.

The method of preparation was as follows. First, about ten liters of whole pomegranate seeds were slowly added to a standard kitchen blender, and were homogenized for about twenty seconds at a low speed, so that the juice was released and the seeds were coarsely crushed. Hereinafter, the term "crushed" also includes chopped, pressed or squeezed.

Preferably, an aqueous extract was prepared next by placing about 300 g of schizandra berries, about 300 g each of Chinese licorice root and Chinese asparagus root, and about 150 g of Chinese angelica root, in a large pot with six liters of distilled water. The ratio of these ingredients was thus about 2:2:1:2 Chinese licorice root to Chinese asparagus root to Chinese Angelica root to schizandra berries. Preferably, the contents were brought to a boil, covered and allowed to simmer for about three hours over a low flame. The mixture was then allowed to cool at room temperature.

The pomegranate seeds and juice were then placed in a sterilized bottle, preferably about five gallons in volume. The aqueous extract was also preferably added to the bottle, forming a mixture. Preferably, about 5 g of wine yeast, most preferably Lapin™ EC-1118, Lallemand Inc., Montreal, Canada, was added to the bottle and a sterile surgical glove affixed to the mouth of the bottle with a rubber band. The bottle was preferably then put in a warm place so that fermentation occurred, which was allowed to proceed to completion, taking approximately ten days. The glove acted as an escape valve to prevent the build-up of gases.

After fermentation, the glove was removed and the contents of the bottle were preferably topped off with an ordinary dry red wine, most preferably Carmel Hilonim™ 1995, Carmel Winery, Israel. About two liters of this wine was added to the bottle. The bottle was then preferably sealed and placed in a cool, dark place for about three months.

After three months, the liquid contents of the bottle, which was the mixture of the pomegranate extract and the aqueous herbal extract, were preferably removed and strained through cheesecloth, leaving solid material in the bottle and forming a filtered extract. The water and alcohol were preferably gradually evaporated by placing the liquid in an uncovered pot over a very low flame, with an asbestos pad between the pot and the flame. After approximately 72 hours, the volume of liquid was reduced to about 10% of its original volume, resulting in a concentrated liquid. This heating process was performed carefully so that the liquid is not overheated and burned during this evaporation.

The concentrated liquid was preferably combined with an equal volume of unrefined bee honey and gently heated for a few minutes. This honey mixture was then placed in a brown glass bottle and set aside.

The solid material from the five-gallon bottle was then preferably placed in another glass bottle and covered with food grade alcohol, so that a second alcohol extract was obtained by contacting the solid material with ethanol. This bottle was then shaken briskly for several minutes twice each day for about three days. Next, the alcohol was preferably decanted and gradually evaporated, leaving a second solid material. Preferably, the evaporation is preformed using a vacuum distillation apparatus, although for this Example the evaporation was performed by heating over a low flame. After evaporation, a syrup was obtained, which was added to the honey mixture in the brown glass bottle.

The second solid material was preferably heated at a high temperature until it burned, for example by placing the solid material in a kitchen oven with a high flame. The resultant black powder was then heated at a high temperature for about 72 hours until the powder was nearly white. Hereinafter, the term "carbonized solid material" includes either the black powder or the white powder, or a mixture thereof.

The carbonized solid material was then preferably added to at least ten times its volume of distilled water and heated almost to boiling for one hour while the mixture was continuously stirred, so that an aqueous extract was obtained by contacting the carbonized solid material with water. The aqueous extract was then preferably filtered through filter paper, and the remaining solid material discarded. This aqueous extract was preferably gradually heated over a low flame, until nearly all of the liquid had evaporated, leaving a concentrated solution of calcined salts.

This concentrated solution of calcined salts was then preferably added to the honey mixture in the brown glass bottle. This final mixture was then preferably gently heated and stirred to form the phytoestrogen supplement.

Alternatively and preferably, the phytoestrogen supplement can be mixed with pomegranate oil prepared according to the following method. First, pomegranate seeds were dried to remove excess moisture. The oil was then extracted from the seeds by pressing the seeds in a hydraulic oil press at room temperature. This oil is then mixed with the phytoestrogen supplement to form a combination of pomegranate oil and phytoestrogen supplement, of which up to about 50% (volume/volume) can be pomegranate oil. This combination is preferably placed in gelcaps as a pharmaceutical preparation, for ease of oral administration.

EXAMPLE 2

Methods of Preparation of Topical Phytoestrogen Supplements

The following botanical materials were used to prepare various embodiments of the topical phytoestrogen supplements: pomegranate material, preferably pomegranate seeds (*Punica granatum*), coconut milk (*Cocus nucifera*), schizandra berries (*Schizandra chinensis*) and Chinese asparagus root (*Asparagus lucidus*). The pomegranate seeds were preferably dried. The schizandra berries were also preferably dried. The Chinese asparagus root was preferably dried and cut. Preferably, the coconut milk was taken from immature coconuts. Most preferably, the coconut milk is combined with the coconut pulp, rapidly frozen at −40 C., dried under vacuum at pressures in a range from about 0.01 to about 1 mbar and then ground into a fine powder. Hereinafter, the term "coconut milk" includes either the liquid milk itself, or the fine powder prepared as described above.

The basis of the phytoestrogen supplements of Example 2 was a mixture of a preparation of the pomegranate material, preferably pomegranate seeds, which were pressed as described below to produce pomegranate oil, and of the coconut milk. Hereinafter, the term "pressed" also includes squeezed and crushed. Preferably, the supplements also included schizandra berries and Chinese asparagus root.

The method of preparation was as follows. First, pomegranate seeds were dried to remove excess moisture. The oil was extracted from the seeds by pressing the seeds in a hydraulic oil press at room temperature.

Preferably, extracts of Chinese asparagus root and schizandra berries were prepared by contacting these materials with food grade ethanol and using exhaustive Sohxtlett extraction. The alcohol was then preferably gradually removed, preferably by vacuum distillation, to form a solid. Alternatively, the extracts were prepared by placing about 500 g of each of these materials in about 4 liters of food grade alcohol contained in a glass vessel, closing the vessel and allowing it to rest in a cool, dark place for four months. In this case, the alcohol was removed by slow evaporation over a low flame with an asbestos pad for about 12 hours.

Preferably, about 15 g of bleached beeswax and about 15 g of cocoa butter were then melted in a warm water bath of about 80° C. These two substances do not contain phytoestrogens, but are added for ease of topical administration, and can form at least a portion of a pharmaceutically appropriate carrier.

About 40 g of pomegranate oil was added to these melted fats and continuously stirred. Next, about 20 g of coconut milk from immature coconuts was added to this mixture. Preferably, this milk was a commercially available canned coconut milk, Chaokoh™, Thep Padung Porn Coconut Co., Bangkok, Thailand. More preferably, the volume of the milk was reduced by about 80% by evaporation over a low flame with an asbestos pad. Most preferably, fresh immature coconut milk is freeze dried and the resulting powder is used.

Preferably, about 3 g of asparagus root extract and of schizandra berry extract were then added to the mixture to form a second mixture. The final ratio of the ingredients in the second mixture was thus about 40:20:3:3 pomegranate oil to coconut milk to extract of Chinese asparagus root to extract of schizandra berries. Preferably, a number of compounds was added to tie second mixture for preservation of the supplement and for ease of topical administration: about 1 g of citric acid, about 1 g of boric acid and about 0.5 g each of methylpropane and of propylparaben. The resultant composition was preferably stirred continuously in the warm water bath for about 20 minutes, and then poured into containers and allowed to cool, forming the finished product for face cream and general skin care, hereinafter referred to as "skin cream".

To prepare an ointment for vaginal application, about 80 g of the cooled mixture was added to about 20 g of hydrophilic lanolin, such as Eucerin™, Beirsdorf Company, Hamburg, Germany, which was added for ease of topical administration and can form at least a portion of an appropriate pharmaceutical carrier. The resultant mixture was then preferably stirred continuously in a warm water bath until uniform and then poured into containers to cool. This product is hereinafter referred to as "vaginal ointment". Hereinafter, the term "ointment" includes the skin cream and vaginal ointment of the present invention.

EXAMPLE 3

Alternative Methods of Preparation of Skin Cream

Skin cream can also be prepared according to one of three alternative methods, using some or all of the botanical materials of Examples 1 and 2.
Alterative Method 1

First, the skin cream of Example 2 was prepared. Next, pomegranate rind extract was added to this skin cream, so that the final concentration of pomegranate rind extract in the skin cream was in the range of about 1% to about 10%, preferably about 3% Preferably, this pomegranate rind extract was prepared by contacting pomegranate rinds with a suitable solvent, most preferably water.

The pomegranate rind extract was prepared as follows. First, rinds and some seeds from the pomegranate fruit were placed in a pressure cooker, filling the cooker to about two-thirds of its full capacity. The contents of the pressure cooker were then covered with water and cooked for about 15 minutes under pressure. The resultant extract was then removed and heated until about 90% of the water was evaporated, to form a concentrated extract, Preferably, this extract is further concentrated by gentle heating for about 24 to about 48 hours to form a further concentrated extract. The farther concentrated extract is then preferably mixed with an equal volume of bee honey.
Alternative Method 2

The following substitution can be made in the skin cream of Example 2. A pomegranate extract can be substituted for a portion of the pomegranate seed oil used in Example 2. This pomegranate extract is prepared by contacting pomegranate seeds and juice with an appropriate solvent, preferably ethanol.

This extract can be prepared by modifying the method of Example 1 to eliminate the addition of botanical material other than the pomegranate seeds and juice. First, about ten liters of whole pomegranate seeds were slowly added to a standard kitchen blender, and were homogenized for about twenty seconds at a low speed, so that the juice was released and the seeds were coarsely crushed. Hereinafter, the term "crushed" also includes chopped, pressed or squeezed.

The pomegranate seeds and juice were then placed in a sterilized bottle, preferably about five gallons in volume. Preferably, about 5 g of wine yeast, most preferably Lapin™ EC-1118, Lallemand Inc., Montreal, Canada, was added to the bottle and a sterile surgical glove affixed to the mouth of the bottle with a rubber band. The bottle was preferably then put in a warm place so that fermentation occurred, which was allowed to proceed to completion, taking approximately ten days. The glove acted as an escape valve to prevent the build-up of gases.

After fermentation, the glove was removed and the contents of the bottle were preferably topped off with an ordinary dry red wine, most preferably Carmel Hilonim™ 1995, Carmel Winery, Israel. About two liters of this wine was added to the bottle. The bottle was then preferably sealed and placed in a cool, dark place for about three months.

After three months, the liquid contents of the bottle, which was the pomegranate extract, were preferably removed and strained through cheesecloth, leaving solid material in the bottle and forming a filtered extract. The water and alcohol were preferably gradually evaporated by placing the liquid in an uncovered pot over a very low flame, with an asbestos pad between the pot and the flame. After approximately 72 hours, the volume of liquid was reduced to about 10% of its original volume, resulting in a concentrated liquid. This heating process was performed carefully so that the liquid is not overheated and burned during this evaporation.

The concentrated liquid was preferably combined with an equal volume of unrefined bee honey and gently heated for a few minutes. This honey mixture was then placed in a brown glass bottle and set aside.
Alternative Method 3

A skin cream is prepared according to Example 2 above, but without the extracts of schizandra and Chinese asparagus. A phytoestrogen supplement is prepared according to Example 1 and is then added to the skin cream as about 6% of the total weight.

EXAMPLE 4

Method of Preparing a Suspension Containing Phytoestrogen Supplement

The following botanical material was used to prepare the phytoestrogen supplement in a suspension according to the present invention: pomegranate material, preferably pomegranate seeds (*Punica granatum*). The pomegranate seeds were preferably fresh with intact juice sacs.

The basis of the phytoestrogen supplement in a suspension of this Example was a preparation of the pomegranate material, preferably pomegranate seeds, which were contacted with an appropriate solvent as described below, preferably including water and ethanol, to form an extract. As described previously for Example 1, the extract was suitable for oral administration, for example by using solvents which were substantially non-toxic to the subject, so that there should not be an untoward level of adverse side effects, such as toxicity, irritation, allergy or hypersensitivity responses. Examples of such substantially non-toxic solvents include water and ethanol.

The method of preparation was as follows. First, an automated Zumex™ juice extraction machine was used to cut and squeeze juice from the pomegranates. The pomegranate seeds were then manually removed from the juiced hulls. These pomegranate seeds and juice were mixed and allowed to ferment. The mixture was then allowed to stand for a period of time ranging from about 7 days to about three months after fermentation. The pomegranate seeds were then removed from the fermented liquid. Ethanol was removed from the fermented liquid by distillation to form a first removed ethanol. Next, the liquid was concentrated to a fluid concentrate by gentle heating. The concentrate was then dried to a powder in a drying oven. Alternatively, the concentrate could have been freeze-dried to form the powder.

Next, the seeds were dried, for example by using a hot air blower or by using a passive solar dryer. The dried seeds were then pressed with a cold press extraction machine to obtain a clear yellow oil, such that a seed cake remained after pressing. This seed cake was extracted with water and the removed ethanol, obtained as described previously, to form a first extract. The removed ethanol and water were preferably in a 1:1 ratio, and the extraction was preferably performed by using a passive cold maceration process. Alcohol (ethanol) was then removed from the first extract by distillation, to form a second removed ethanol. The remaining liquid was then dried to form a second powder by using gentle heat, preferably in a drying oven.

The previously extracted seed cake was then extracted by using a mixture of the first and second removed ethanol and water, in a ratio of 80:20 alcohol:water, by using a Sohxtlett extractor to form a second extract. Alcohol (ethanol) was then removed from the second extract by distillation, to form a third removed ethanol. The remaining liquid was then dried to form a third powder by using gentle heat, preferably in a drying oven.

The clear yellow oil from the pressed seed cake was then combined with the first, second and third powders to create a suspension according to the present invention. Optionally and preferably, the pomegranate seed oil was mixed with barley seed oil before being mixed with the powders. The suspension was preferably placed in a gel cap for administration of the pomegranate supplement.

EXAMPLE 5

Methods of Preparation of Nutraceutical Supplements

The following botanical materials are used to prepare various embodiments of the phytoestrogen supplement: pomegranate material, preferably pomegranate seeds (*Punica granatum*), more preferably prepared as pomegranate seed oil; barley material, preferably including barley seed oil and optionally including barley seed cake; cherry kernel material, preferably including cherry kernel oil; and fenugreek material, preferably including fenugreek seed oil. The pomegranate seeds are preferably fresh with intact juice sacs.

The basis of the phytoestrogen supplement of this Example is the preparation of seed oil from the various types of seeds listed above. Preferably, the seed oil is prepared by cold pressing the seeds, such that the seed oil is obtained and a seed cake remains. More preferably, the seed oil is a combination of pomegranate seed oil and at least one other seed oil listed previously. Most preferably, the seed oil includes all of these seed oils, such that the seed oil is a combination of pomegranate seed oil; barley seed oil; cherry kernel oil; and fenugreek seed oil. In this latter form, the seed oil is a nutraceutical oil blend.

Barley is a particularly advantageous component of the seed oil combination of the present invention, since barley seed oil has been shown to inhibit cholesterol biosynthesis and to enhance immunologic function in animals [Babu et al., *Annals of New York Academy of Science*, 669:317–319, 1992]. Barley seed oil contains certain compounds, including leukoktienes and other tocopherols, which may be important physiologically. Other factors in barley may aid in the treatment of diabetes [*Journal of American Dietetic Association*, 95:749, 1995; Madhi et al., *Annals of Nutrition and Metabolism*, 35:65–70, 1991. Madhi et al., *American Journal of Clinical Nutrition*, 61:614–15, 1995]. Also, barley has been used in traditional Chinese medicine for centuries.

Similarly, fenugreek has been shown to have beneficial effects in the treatment of diabetes [Petite et al., *Steroid*, 60:674–680, 1995]. Fenugreek is also a rich source of diosgenin, which is a precursor for a number of different hormones, including estrogen, testosterone and progesterone [Aradhana et al., *Indian Journal of Experimental Biology*, 30:367–370, 1992]. Cherry kernels also have medicinally useful properties [Price et al., *Food Additives and Contaminants*, 2:73–106, 1985].

The seed oil, and particularly the nutraceutical oil blend, is optionally administered in a variety of ways, including but not limited to, oral and topical administration. Preferably, topical administration includes administration as a face and/or body cream for dermatological and/or cosmetic purposes, as well as a vaginal ointment to protect against or to alleviate vaginal dryness and dyspareunia.

As another optional but preferred embodiment, the seed cake which remains after cold pressing the seeds is used to prepare nutraceutical foods. For example, the barley seed cake (the seed cake which remains after pressing barley seeds) can be optionally and preferably used to prepare barley bars, breads, cakes, crackers, pastas and cakes, for example. These may be useful for individuals with diabetes who are being maintained on hypoglycemic medications and/or diet treatments, A combination of barley seed cake with pomegranate seed cake and/or fenugreek seed cake is more preferred, since such a combination would enhance not only the efficacy of the cake for the treatment of diabetes, but would also provide desirable hormonal effects. Thus, this embodiment of the present invention would have a number of different desirable effects.

EXAMPLE 6

Methods of Administration of Phytoestrogen Supplements

The phytoestrogen supplement prepared according to the methods in Examples 1, 2, 3 and 5 can be administered to a patient in a number of ways, which are well known in the art. For example, administration may be done topically (including opthalmically, vaginally, rectaly, intranasally), orally, by inhalation, or parenterally, for example by intravenous drip or intraperitoneal, subcutaneous, or intramuscular injection.

Preferably, the phytoestrogen supplement prepared according to Examples 1 or 5 are administered orally, and the phytoestrogen supplement prepared according to Examples 2, 3 or 5 are administered topically. Most preferably, the skin cream prepared according to Examples 2, 3 or 5 is administered to the skin of the patient, including but not limited to, the skin of the hands and face, and the vaginal ointment prepared according to Examples 2 or 5 is administered to the vagina of the patient.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the patient to the phytoestrogen supplement. Persons of ordinary skill in the art can easily determine optimum dosages, dosing methodologies and repetition rates.

EXAMPLE 7

Case Histories of Treatment with Oral Phytoestrogen Supplements

Each of the following patients was treated with the phytoestrogen supplement prepared according to the most preferred embodiments of Example 1.

Case History 1

A fifty-two year old female reported a chief complaint of hot flashes which she felt over her entire body and which left her drenched in sweat. Each episode of hot flashes lasted about two minutes and recurred as often as ten times per day. These hot flashes had started about two months previously. Prior to the onset of these symptoms, her menses had been irregular and infrequent for about two years, and had ceased entirely over the previous two months. The patient was given 2 ml of the oral phytoestrogen supplement, prepared according to Example 1 above, to be taken three times a day. Within 24 hours, the patient reported that the hot flashes had almost ceased entirely. The patient continued taking the supplement daily for two weeks. During this period, a few hot flashes did occur, but these were of markedly less intensity. After several weeks, the symptoms did return, but were considerably more mild and less frequent than before treatment.

Case History 2

A fifty-four year old female complained of hot flashes since the cessation of her menses two years previously. Recently, the symptoms had increased both in intensity and frequency, and were occurring up to twenty times a day. After treatment three times a day for a two week period with 0.5 cc of the oral phytoestrogen supplement, prepared according to Example 1 above, the patient reported that the hot flashes had decreased in frequency to only about 3–4 times a day, were of shorter duration and considerably lower intensity. This improvement seemed to be permanent, even after the patient stopped taking the oral phytoestrogen supplement after about two months of treatment.

Case History 3

A forty-eight year old female reported feelings of depression and lack of interest in her usual activities after the cessation of her menses, two years previously. Also, she had difficulty controlling food cravings for chocolate, and would eat large amounts of chocolate at a single sitting. After treatment once a day with 0.5 cc of the oral phytoestrogen extract, prepared as in Example 1 above, she reported a significant amelioration of her depression and a concomitant decrease in her cravings for chocolate. The effect was noticeable after two weeks of treatment, and was also noticeable even six months after treatment, so the effect appeared to be permanent.

EXAMPLE 8

Case Histories of Treatment with Topical Phytoestrogen Supplements

Each of the following patients was treated with the phytoestrogen supplement prepared according to the most preferred embodiments of Example 2, except that evaporated, liquid coconut milk was used instead of the fine powder.

Case History 1

A forty-five year old female complained of wrinkled facial skin. After two weeks of applying the skin cream prepared according to the method of Example 2, the patient reported that her skin bad greater elasticity and turgor and that her skin was less wrinkled. The patient also reported that the cream had a pleasant feel.

Case History 2

A seventy three year old female applied the skin cream, prepared according to the method of Example 2, to the skin on her face and on the backs of her hands. After one week, the patient felt that the skin of her hands and face "looked younger".

Case History 3

A forty eight year old female reported vaginal dryness and associated dyspareunia. She had been on oral estrogen replacement therapy since the age of thirty six, after a therapeutic hysterectomy and oophorectomy for severe fibroids. After applying the vaginal ointment prepared according to the method of Example 2 to her vagina once a day for a two week period, the patient experienced a general amelioration of both the dryness and the dyspareunia. In addition, the patient felt that her condition was "at least a little better" even one month after the two week trial period.

Case History 4

A forty year old regularly menstruating female physician with a benign past medical history complained of oily skin. She applied the skin cream prepared according to Alterative Method 1 of Example 3, with 3% pomegranate rind extract, to her skin for a two week period. She reported a very positive effect, encompassing not only a marked reduction of the excess skin oil to about one-half of former levels, but also improved turgor, elasticity and texture. She felt that the improvement ended about one month after the two week trial, but expressed a desire to resume treatment.

While the invention has been described with respect to a limited number of embodiments, it will be appreciated that many variations, modifications and other applications of the invention may be made.

What is claimed is:

1. A method of preparing a phytoestrogen suspension from pomegranate material, the pomegranate material including seeds, the method comprising the steps of:
   (a) fermenting the pomegranate material to form a fermented pomegranate material;
   (b) removing the seeds from said fermented pomegranate material;
   (c) pressing the seeds to form pomegranate seed oil and a seed cake;
   (d) removing ethanol from the fermented pomegranate material to form a first liquid;
   (e) drying said first liquid to form a first powder; and
   (f) combining said first powder and said pomegranate seed oil to form the phytoestrogen suspension.

2. The method of claim 1, further comprising the step of:
   (g) adding a pharmaceutically appropriate carrier to the phytoestrogen suspension.

3. The method of claim 1, further comprising the step of:
   (g) placing the phytoestrogen suspension in a gel cap.

4. The method of claim 1, wherein step (f) further comprises the step of:
   (i) mixing said pomegranate seed oil with barley seed oil to form mixed oil; and
   (ii) combining said first powder and said mixed oil to form the phytoestrogen suspension.

* * * * *